United States Patent [19]

Whisler et al.

[11] 4,421,121

[45] Dec. 20, 1983

[54] METHOD AND APPARATUS FOR OBTAINING A NON-CEPHALIC REFERENTIAL ELECTROENCEPHALOGRAM

[76] Inventors: John W. Whisler, 1489 Albert St. North, Saint Paul, Minn. 55108; Walter J. Re Mine, 783 Iglehart Ave., Saint Paul, Minn. 55104

[21] Appl. No.: 193,832

[22] Filed: Oct. 3, 1980

[51] Int. Cl.³ .............................................. A61B 5/04
[52] U.S. Cl. ................................................... 128/731
[58] Field of Search ................................ 128/731, 732

[56] References Cited
U.S. PATENT DOCUMENTS 3,826,243 7/1974 Anderson ............................. 128/732
4,092,981 6/1978 Ertl ....................................... 128/731

FOREIGN PATENT DOCUMENTS 2016706 9/1979 United Kingdom ................ 128/731

OTHER PUBLICATIONS

Plumb et al., "IEEE Transactions on Biomedical Engineering", Oct. 1964, vol. 11, No. 4, pp. 157-159.

Primary Examiner—William E. Kamm

[57] ABSTRACT

A method and apparatus to provide an electroencephalogram (EEG) measured with respect to a reference which is not on the head and to eliminate the electrocardiographic (EKG) artifact which normally contaminates such a measurement. At least three electrodes are placed at or below the base of the neck. Signals from these electrodes are linearly combined, thereby producing a reference signal. The reference signal is then subtracted from signals derived from scalp electrodes. The linear coefficients are adjusted to eliminate the EKG artifact.

9 Claims, 1 Drawing Figure

METHOD AND APPARATUS FOR OBTAINING A NON-CEPHALIC REFERENTIAL ELECTROENCEPHALOGRAM

SUMMARY OF THE INVENTION

It is desired to measure the electroencephalogram (EEG) on the scalp with respect to a reference which is not on the head. However this typically results in large amounts of electrocardiogram (EKG) artifact in the measured EEG. This invention concerns itself with a method and apparatus for measuring the EEG against a reference which is not on the head and in addition results in EEG data which is relatively free of EKG. This is achieved by synthesizing a reference signal (measured against a ground) and then subtracting this same reference signal from each of the scalp signals (measured against the same ground). This reference signal is synthesized as a linear combination of several signals derived from several reference electrodes where these reference electrodes are not on the head.

SPECIFICATION AND DESCRIPTION OF THE INVENTION

Figure 1:
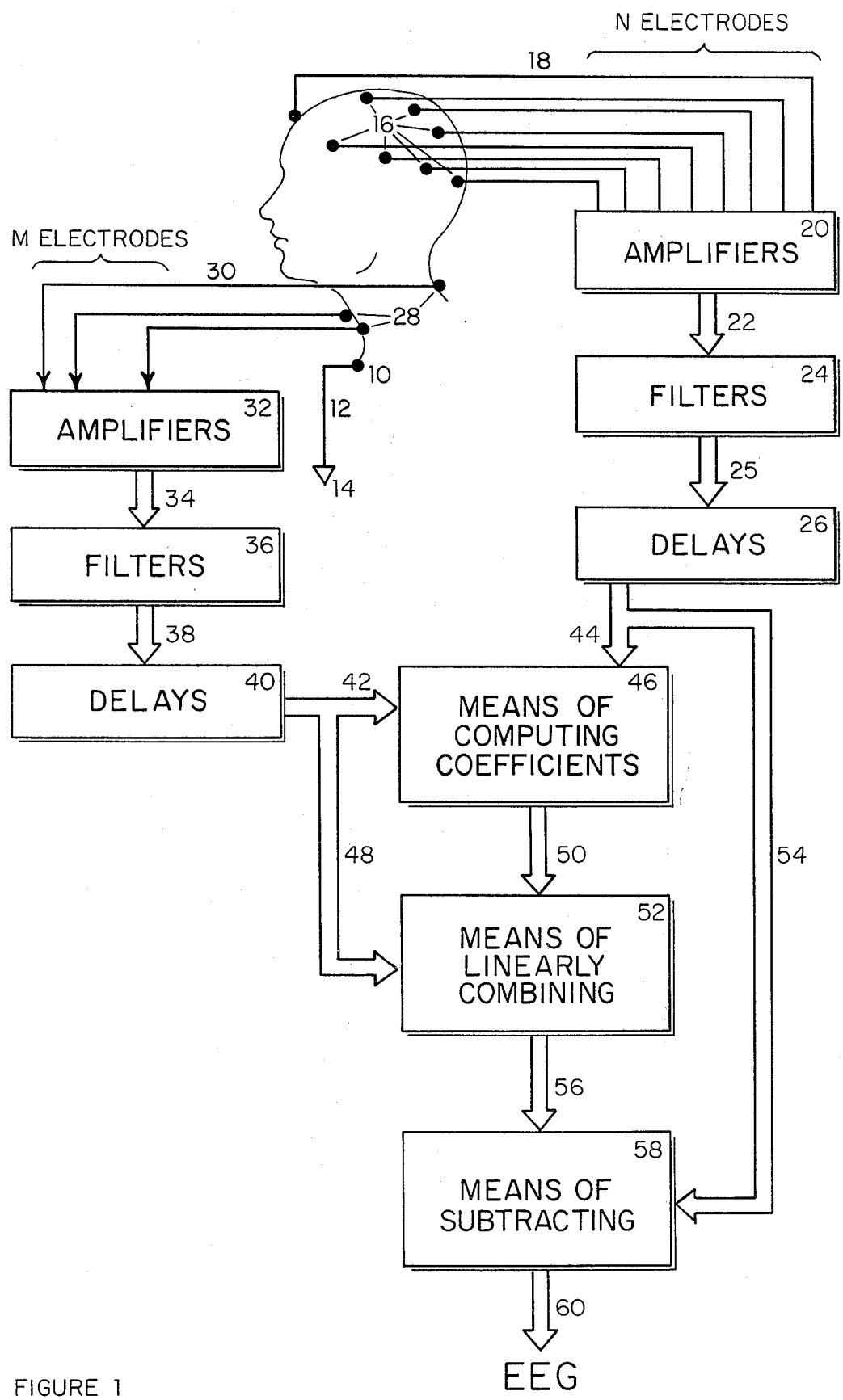
FIG. 1 illustrates a block diagram of the system for obtaining electroencephalographic signals with a non-cephalic reference electrode arrangement utilizing a means of computing coefficients, means of filtering, and means of delaying.
Figure 2:
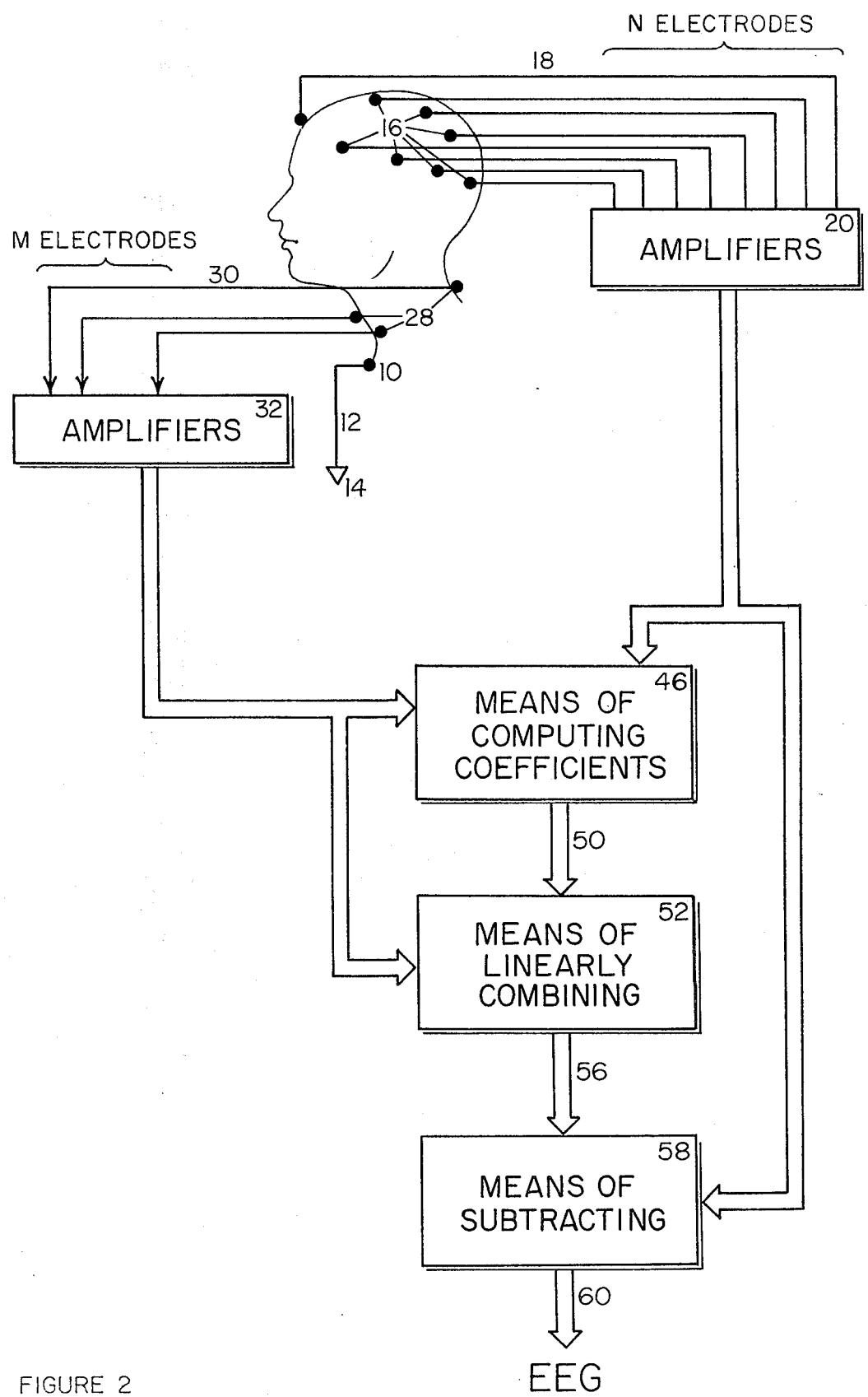
FIG. 2 illustrates a block diagram of the system for obtaining electroencephalographic signals with a non-cephalic reference electrode arrangement utilizing a means of computing coefficients.
Figure 3:
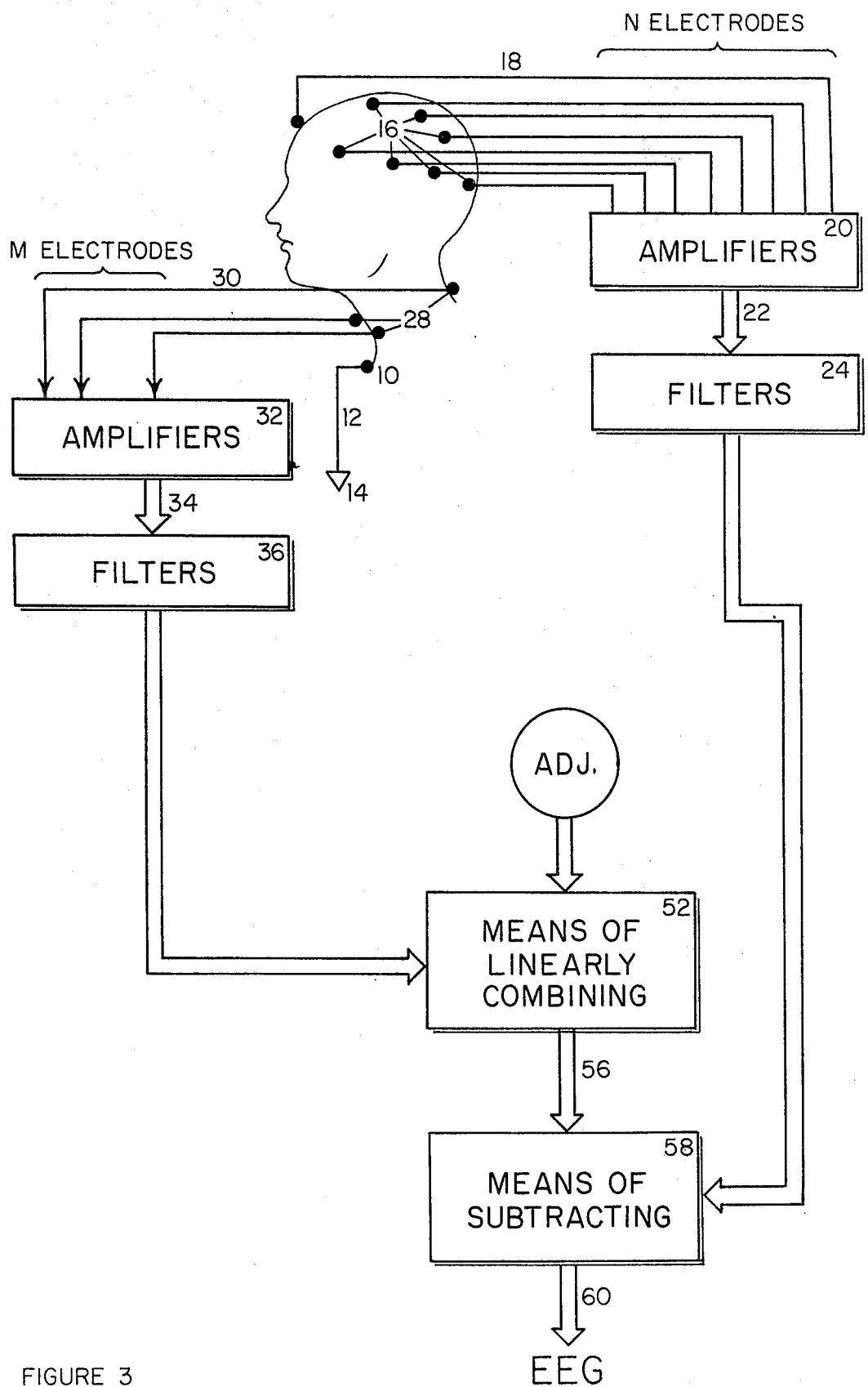
FIG. 3 illustrates a block diagram of the manually adjusted system for obtaining electroencephalographic signals with a non-cephalic reference electrode arrangement utilizing means of filtering.

The invention comprises a method and apparatus for obtaining an electroencephalogram (EEG) and is shown in FIG. 1. The ground or common electrode means (10) is placed on the body at or below the base of the neck preferably on the upper end of the sternum. All the signals herein described are measured with respect to this ground or common electrode means (10). There is a conductive means (12) which connects the ground or common means (10) to the circuit ground or common (14). There are N electrode means (16) on the scalp of the subject where N is the number of electrode means (16). N is typically sixteen to twentyfive. There are N conductive means (18) for making N one to one connections between the N electrode means (16) and the inputs of N amplifier means (20). There are communication means (22) for getting the outputs of the N amplifier means (20) to the inputs of N filter means (24) on a one to one basis. These filter means (24) and (36) are linear and are used to alter the waveshape of the data that passes through them. The filter means (24) and (36) are also used to eliminate components of the data which are of no interest to the operator. Some examples of undesirable signals would be dc and low frequency components, sixty hertz hum, and frequencies over 100 hertz. There are communication means (25) for getting the outputs of the N filter means (24) to the inputs of N delaying means (26) on a one to one basis.

There are M electrode means (28) where M is three or more. These M electrode means (28) are placed at or below the base of the neck. When M is three the electrode means (28) are placed preferably one on the seventh cervical vertebra and one at the midpoints of each of the right and left clavicles. The M electrode means (28) and the ground or common electrode means (10) are preferably the self-adhesive EKG electrodes of the type used for stress testing. They can also be the dome or disk type EEG electrodes attached with collodion. Other types of electrodes may also be used. The N electrode means (16) are preferably the dome or disk type EEG electrodes attached with collodion although other types may be used. Some of the N electrode means (16) may be sphenoidal and/or nasopharyngeal electrodes. There are M conductive means (30) which make a one to one connection between the M electrode means (28) and the inputs of M amplifier means (32). Everything that comes after the amplifier means (20) and (30) may be realized in either analog or digital nature and the communications means (22), (25), (34), (38), (42), (44), (48), (50), (54), (56), and (60) will perform the necessary analog to digital and digital to analog conversions. There are communication means (34) for getting the outputs of the M amplifier means (32) to the inputs of M filter means (36) on a one to one basis. There are communications means (38) for getting the outputs of the M filter means (36) to the inputs of M delaying means (40) on a one to one basis.

There are communications means (48) for getting the outputs of the M delaying means (40) to the inputs of a means of linearly combining (52). This means of linearly combining (52) may be realized for example by a network of potentiometers, resistors, and amplifiers. The means of linearly combining (52) could also be realized with either analog or digital multipliers together with a means of summing the outputs of the multipliers. It could also be realized with multiplying digital to analog converters together with a means for summing. There are many of these realizations for a means of linearly combining which are straightforward and common engineering practice. This means of linearly combining (52) will output N channels of data, each of which is a linear combination of the M channels of data that are received through communications means (48). There are M real linear coefficients $C1, C2, C3, \ldots, CM$ for each of N channels of time varying data. There are therefore M times N coefficients.

There are communications means (56) for getting the output of the means of linearly combining (52) to the N subtrahend inputs of N means of subtracting (58). There are communications means (54) for getting the output of the N delaying means (26) to the N minuend inputs of the said N means of subtracting (58). These said N means of subtracting will each have one output. Therefore there will be N outputs where each output is the result of subtracting one channel of data in (56) from a corresponding channel of data in (54). The N outputs of the said N means of subtracting (58) are then conveyed to the user through communications means (60).

Figure 4:
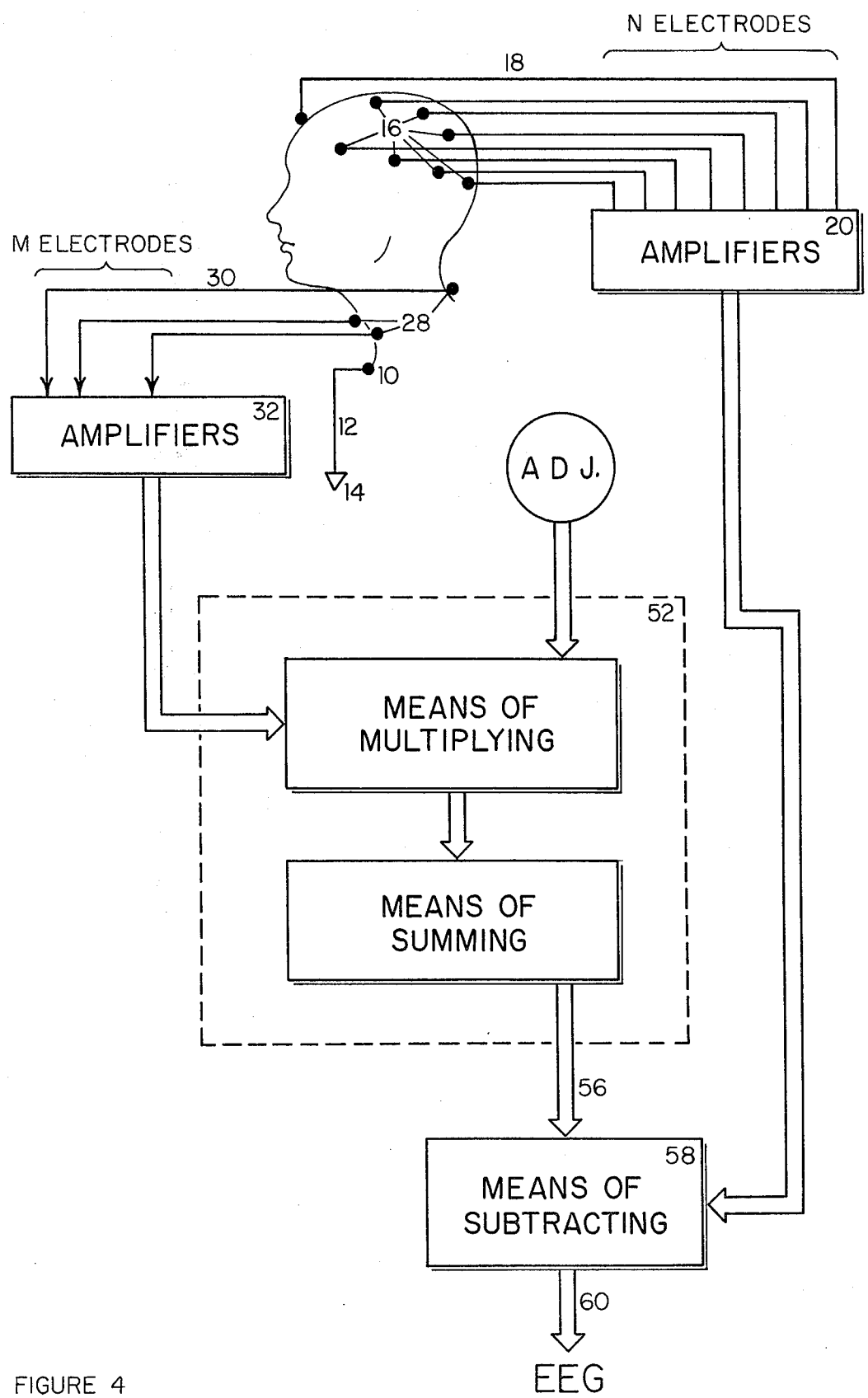
FIG. 4 illustrates a block diagram of the manually adjusted system for obtaining electroencephalographic signals with a non-cephalic reference electrode arrangement.

The N filter means (24), N delaying means (26), and N means of subtracting (58) are not necessarily each composed of N subassemblies of apparatus. Refer to FIG. 4 for details of the means of linearly combining (52). For example, N subtraction units are not necessarily required to perform the N means of subtracting (58) because the data can be multiplexed and processed through one subtraction unit. The same holds true for the M filter means (36) and the M delaying means (40), and for the means of linearly combining (52) of the M channels of data that come through communications means (52).

The output data from said communications means (60) contains useful electroencephalographic information when the method is properly applied, the hardware is properly adjusted and suitable linear coefficients have been found. To find these coefficients there are communications means (42) for getting the M outputs of the M delaying means (40) to a first input of a means for computing coefficients (46). There are communications means (44) for getting the N outputs of the N delaying means (26) to a second input of said means of computing coefficients (46). Said means of computing coefficients computes M times N linear coefficients which are optimum (using some criteria) and outputs them through the communications means (50) to the means of linearly combining (52).

In a simplified embodiment, the number of coefficients which must be computed and the number of means of linearly combining (52) can each be reduced by a factor of N with little reduction in the performance of the method. This is because most human subjects the EKG artifact on the scalp is relatively equipotential over the whole scalp. Therefore the EKG artifact which must be subtracted using the means of subtracting (58) can be approximated as being identical for each of the N channels. Therefore the means of linearly combining (52) will only have to output one channel of data instead of N channels of data. Likewise the means of computing coefficients (46) will only have to compute M linear coefficients instead of M times N. By using this approximation the amount of complexity and hardware can be reduced. This approximation will be assumed for the remainder of the discussion and reference will therefore only be made to a means of computing one set of M linear coefficients. However the same means of computing coefficients (46) described herein may likewise be applied to N sets of M linear coefficients.

The amplifier means (20) and (32), the filter means (24) and (36), and the delaying means (26) and (40) are all adjustable, and these should be adjusted to give the best results. For example, the gain of the amplifier means (20) and (32) should be set to maximize the signal to noise ratio and to make best use of the available dynamic range of the apparatus. The N filter means (24) should not be set so as to alter or distort the component of the EEG data which the user desires. This alteration can happen because the EEG data passes through these filter means (24).

For the remainder of this description call the M channels of data passing through the communications means (42) and (48) the "reference signals", call the N channels of data passing through the communications means (44) and (54) the "scalp signals", call the channel of data passing through the communications means (56) the "non-cephalic reference signal", and call the N channels of data passing through the communications means (60) the electroencephalogram (EEG). These reference, scalp, and EEG signals may be in any analog or digital representation.

The filters means (24) and (36), delaying means (26) and (40), and the M linear coefficients should be adjusted so that there is as little as possible EKG artifact in the EEG. These adjustments should make the EKG artifact in the non-cephalic reference signal as similar as possible to the EKG artifact in the scalp signals because then the common EKG artifact may be subtracted out using the means of subtracting 58.

There are several means for making the EKG artifact in the non-cephalic reference signals similar to the EKG artifact in the scalp signals. They may be made similar in amplitude by adjusting the M linear coefficients for the means of linearly combining (52). They may be made similar in time (i.e. synchronous) by adjusting the delaying means (26) and (40). Finally they may be made similar in waveshape by adjusting filter means (24) and (36). These adjustments should all be made with the final objective of reducing the residual EKG artifact in the EEG.

It should be pointed out that some of these adjustments are interrelated. That is to say a change in one adjustment may to some extent undo a the result of a change in another adjustment. For example a change in the amount of residual EKG artifact due to a filter means (36) adjustment might be undone by an adjustment in delaying means (40) because some filters effectively delay input signals that are in the passband of the filter. Because these adjustments can be interrelated manual adjustment procedures can sometimes be difficult. However for many human subjects the delaying means (26) and (40) and the filter means (24) and (36) are not required in order to get adequate EKG artifact reduction. Therefore, only the M linear coefficients (required by the means of linearly combining (52)) which must be adjusted. Since three reference electrodes are frequently adequate for good EKG cancellation only three linear coefficients need to be found and therefore the amount of adjustment that is typically required is reduced.

These adjustments depend on the criteria that are being used to define the amount of residual EKG in the EEG. For example, one criteria that the operator may desire to use to define to amount of residual EKG is the statistical mean of the peak to peak amplitude of the QRS wave in the EEG. The operator may then adjust the apparatus so as to minimize the the amount of residual EKG (as defined and measured by using this criteria). Another criteria which the operator may desire to use is the statistical correlation between the EEG and the reference signals (which presumably contain no EEG). The operator may then adjust the apparatus so as to minimize the residual EKG (as defined and measured by using this second criteria). It is likely that the two criteria will produce to two different adjustments of the apparatus. An alternate criteria is the statistical correlation between the scalp signals and the reference signals. The coefficients can be adjusted to maximize this correlation thereby minimizing the residual EKG (as defined and measured by this criteria). Many more such criteria are possible. Several such criteria and adjustment methods will now be discussed.

The operator of the apparatus may use his own criteria (whatever it may be) for determining the amount of EKG artifact present in the EEG. The operator may then manually adjust the various components of the apparatus to reduce the amount of residual EKG artifact until the artifact is at an acceptable level. In this case the operator is the means of computing coefficients (46). In this method it may be helpful for the operator to have knowledge of the reference signals and the scalp signals. The operator gets this knowledge through communications means (42) and (44) respectively and as before the operator continues to get the EEG data through communications means (60). These communications means (42) and (44) may be pen writeouts on a chart recorder for example. With this knowledge of the data and a knowledge of how the various adjustments affect the residual artifact (as described previously) and criteria (which the operator provides) the operator can minimize the residual EKG artifact in the EEG to his satisfaction.

Another example would be the following. The operator can again use his own criteria, but with additional apparatus to help him make measurements on the reference, scalp, and EEG signals. The results of these measurements can help him make the necessary adjustments. For example, apparatus for measuring the time skew between the peak of QRS waves in the reference signals and the peak of corresponding QRS waves in the scalp signals aids the operator in adjusting the delaying means (26) and (40). By using these measurements the operator can adjust the delaying means (26) and (40) until the statistical mean of the measured skews is zero. Similarly, apparatus to measure the correlation coefficients between the reference signals and the scalp signals can be used. The operator adjusts delay means (26) and (40) so that said correlation coefficients are maximized. This method is most effective when the correlation coefficients are measured over the QRS interval. Storage oscilloscopes or chart recorders can be used to aid the operator in adjusting the filter means (24) and (36). The operator can use oscilloscopes and chart recorders to display the QRS waveforms in the reference and scalp signals. The operator can then adjust the filter means (34) and (36) until the average QRS waveform is the same for all these signals. As stated previously, when the operator makes this adjustment he should avoid distorting the EEG data that he desires. This can occur if the operator improperly adjusts filter means (24).

Another method of adjusting the M linear coefficients is to use a computer as the means for computing coefficients (46). All of the reference, scalp, and EEG signals are known to the computer and the computer can make measurements on this data. The computer can then be programmed with the operator's criteria for defining and measuring the amount of EKG present in the EEG. The computer also contains the hardware required to make the necessary measurements. The computer can also be programmed with the algorithm that the operator wants the computer to use to minimize the measured amount of residual EKG artifact. In this way the computer has the data, criteria, and algorithms for it to compute or search for the M linear coefficients.

We claim:

1. A method for obtaining the electroencephalogram (EEG) which involves,

I. attaching an electrode means (10) at or below the base of the neck,
connecting the electrode means (10) to circuit ground or common (14),
attaching at least three electrode means (28) at or below the base of the neck,
connecting each electrode means (28) to an amplifying means (32),
attaching electrode means (16) to the head of the subject,
connecting the electrode means (16) to amplifying means (20), II. then,
linearly combining the output signals of amplifying means (32) by multiplying each output of said amplifying means (32) by a separate adjustable coefficient and summing the results of said multiplications, thereby producing a reference signal,
and subtracting said reference signal from the output signals of amplifying means (20) thereby obtaining the EEG, and III. adjusting the said adjustable coefficients to reduce the electrocardiographic artifact in the EEG.

2. The method of claim 1 which involves,
attaching the electrode means (10) near the upper end of the sternum,
attaching one of the electrode means (28) on the seventh cervical vertebra,
attaching one of the electrode means (28) at the midpoint of the left clavicle,
and attaching one of the electrode means (28) at the midpoint of the right clavicle.

3. The method of claim 1 where step III comprises computing the coefficients of the linear combination which maximize the statistical correlation between the outputs of amplifying means (20) and the reference signal, and setting the adjustable coefficients to the computed values.

4. The method of claim 1 where step III comprises computing the coefficients of the linear combination which minimize the statistical correlation between the EEG and the reference signal, and setting the adjustable coefficients to the computed values.

5. In an apparatus for obtaining the electroencephalogram (EEG) wherein amplifying means are electrically connected to suitable electrodes, the improvement comprising,
an adjustable means of linearly combining (52) connected to the outputs of at least three amplifying means (32),
the adjusting means of linearly combining (52) multiplies each output of said amplifying means (32) by a separately adjustable coefficient and sums the results of said multiplications, thereby producing a reference signal which is a linear combination of the output signals of said amplifying means (32),
in which said adjustable coefficients are adjustable during operation of the apparatus,
a means of subtracting (58) connected to the outputs of amplifying means (20) and the adjustable means of linearly combining (52), the means of subtracting (58) subtracts said reference signal from the output signals of amplifying means (20) thereby obtaining the EEG.

6. The apparatus of claim 5 with the addition of a means of computing coefficients (46) connected to the outputs of said amplifying means (32), and connected to the outputs of amplifying means (20),
the means of computing coefficients (46) makes measurements on the outputs of said amplifying means (32) and (20), computes from said measurements one coefficient for each of said amplifying means (32), and adjusts the adjustable means of linearly combining (52) so that the computed coefficients are used to produce the reference signal,
the means of comprising coefficients (52) is programmed with an algorithm to compute coefficients which minimize EKG artifact in the EEG.

7. The apparatus of claim 6 with the addition of operator adjustable linear filter means (24) connected to the outputs of amplifying means (20), operator adjustable delaying means (26) connected to the outputs of said operator adjustable linear filter means (24), operator adjustable linear filter means (36) connected to the outputs of amplifying means (32), and operator adjustable delaying means (40) connected to the outputs of said operator adjustable linear filter means (36).

8. The apparatus of claim 5 in which the adjustable means of linearly combining (52) is manually adjustable by the operator.

9. The apparatus of claim 8 with the addition of operator adjustable linear filter means (24) connected between amplifying means (20) and the means of subtracting (58), and with the addition of operator adjustable linear filter means (36) connected between amplifying means (32) and the adjustable means of linearly combining (52).

* * * * *